United States Patent [19]

Desmond et al.

[11] Patent Number: 4,568,698

[45] Date of Patent: Feb. 4, 1986

[54] NOVEL CATALYSTS AND THEIR PREPARATION AND PROCESS FOR THE PRODUCTION OF SATURATED GASEOUS HYDROCARBONS

[75] Inventors: Michael J. Desmond, Cleveland Heights; Marc A. Pepera, Northfield Center, both of Ohio

[73] Assignee: The Standard Oil Company, Cleveland, Ohio

[21] Appl. No.: 652,893

[22] Filed: Sep. 21, 1984

Related U.S. Application Data

[62] Division of Ser. No. 453,474, Dec. 27, 1982, Pat. No. 4,504,590.

[51] Int. Cl.$^4$ ............................................. C07C 1/04
[52] U.S. Cl. ................................. 518/713; 518/714; 518/716; 518/717; 518/719; 518/720; 518/721; 48/197 R
[58] Field of Search ............... 518/713, 714, 715, 716, 518/717, 719, 721, 720; 48/197 R

[56] References Cited

U.S. PATENT DOCUMENTS

| | | | |
|---|---|---|---|
| 3,271,418 | 9/1966 | Plank et al. | 208/120 |
| 3,775,501 | 11/1973 | Kaeding et al. | 260/673 |
| 4,024,171 | 5/1977 | McArthur | 518/715 |
| 4,086,262 | 4/1978 | Chang et al. | 260/449.6 |
| 4,131,568 | 12/1978 | Bartish | 502/74 |
| 4,269,783 | 5/1981 | Brennan et al. | 518/718 |
| 4,276,438 | 6/1981 | Chu et al. | 585/467 |
| 4,278,827 | 7/1981 | Chu et al. | 585/467 |
| 4,279,830 | 7/1981 | Haag et al. | 518/700 |
| 4,294,725 | 10/1981 | Fraenkel et al. | 518/715 |

*Primary Examiner*—Howard T. Mars
*Attorney, Agent, or Firm*—Salvatore P. Pace; David J. Untener; Larry M. Evans

[57] ABSTRACT

Catalysts comprising a medium to large port zeolite modified by the oxide or acid of an element selected from the group consisting of Group IIIA to VIIA elements and, a Fischer-Tropsch catalyst wherein the ratio of zeolite to Fischer-Tropsch component is from about 0.1 to 50:1 can be employed to produce fuel grade saturated gaseous hydrocarbons from synthesis gas. A process is employed which includes the step of contacting synthesis gas over the foregoing catalyst at a reaction temperature of from about 100° C. to 500° C. and at a pressure of from about one atmosphere (0.1 MPa) to about 200 atmospheres (20 MPa) and at a gas hourly space velocity of from about 10 to 100,000. A method is also provided for the preparation of the combination catalyst. The catalyst and process for its use results in a small liquid aromatic product also being formed which is suitable for forming gasoline. Olefins and oxygenates are essentially eliminated.

15 Claims, No Drawings

NOVEL CATALYSTS AND THEIR PREPARATION AND PROCESS FOR THE PRODUCTION OF SATURATED GASEOUS HYDROCARBONS

This application is a division of application Ser. No. 435, 474, filed Dec. 27, 1982, now U.S. Pat. No. 4,504,590.

TECHNICAL FIELD

The present invention is directed toward the production of fuel grade hydrocarbons from synthesis gas. The catalysts and process disclosed are particularly suited for the production of saturated gaseous products in the $C_1$ to $C_5$ range. A small amount of liquid hydrocarbons also results and these comprise almost exclusively high octane gasoline. Regarding the gaseous products, $C_2$ to $C_4$ hydrocarbons are useful in liquid petroleum gas; the products can also be used to produce feedstocks for other chemicals and, they can be employed as reformer feedstocks. A method for the synthesis of the catalysts is also provided.

BACKGROUND ART

The conversion of synthesis gas via Fischer-Tropsch catalysts is a well known process. Such catalysts generally produce liquid products which include components such as organic acids, aldehydes, alcohols and olefins which are undesirable for use as fuels. It is also known to employ zeolite catalysts for the conversion of various organic compounds. For example, U.S. Pat. Nos. 4,276,438 and 4,278,827 disclose processes for the conversion of aromatic compounds to dialkylbenzene compounds. Each process requires a particular type of zeolite catalyst which has been modified with either a Group IB or a Group IVB metal.

U.S. Pat. No. 3,775,501 discloses a process for the production of aromatics from hydrocarbons and air over a zeolite catalyst. U.S. Pat. No. 3,271,418 discloses a process for cracking petroleum gas oil to produce high octane gasoline over a zeolite catalyst where the original alkali metal has been replaced by other cations.

Others have disclosed the use of Fischer-Tropsch catalysts with zeolites in organic synthesis. U.S. Pat. No. 4,279,830, for instance, discloses a two reactor process for converting synthesis gas to oxygenates and hydrocarbons by reducing CO in the first reactor over a Fischer-Tropsch catalyst, where a zeolite is optionally present, followed by treatment in the second reactor over a zeolite catalyst.

U.S. Pat. No. 4,269,783 discloses a process for the conversion of synthesis gases to hydrocarbon mixtures such as olefinic naphtha with an aromatic content of less than 20 weight percent. The olefin plus aromatic content of such products comprises at least 50 weight percent. The zeolite component of the catalyst combination comprises not more than 0.5 weight percent alkali metal.

Lastly, U.S. Pat. No. 4,086,262 discloses a method for the conversion of synthesis gas to hydrocarbon mixtures rich in aromatics. A heterogeneous catalyst comprising zeolites and Fischer-Tropsch synthesis catalysts is employed.

Thus, while the art provides catalysts and processes for the conversion of synthesis gases and other organic feedstocks to various hydrocarbons over mixtures of zeolite and Fischer-Tropsch catalysts, it has not disclosed the specific production of saturated gaseous hydrocarbons.

DISCLOSURE OF INVENTION

It is therefore an object of the present invention to provide a process for producing saturated gaseous hydrocarbons from synthesis gas.

It is another object of the present invention to provide a novel catalyst for converting synthesis gas to saturated gaseous hydrocarbons.

It is still another object of the present invention to provide a method for the preparation of a combination catalyst for the conversion of synthesis gas to saturated gaseous hydrocarbons.

These and other objects, together with the advantages thereof over the prior art, which shall become apparent from the specification which follows, are accomplished by our invention as hereinafter described and claimed.

The catalyst of the present invention comprises a medium to large port zeolite modified by the oxide or acid of an element selected from the group consisting of Group IIIA to VIIA elements and, a Fischer-Tropsch catalyst wherein the ratio of zeolite to Fischer-Tropsch component is from about 0.1 to 50:1.

The process of the present invention produces fuel grade saturated gaseous hydrocarbons from synthesis gas and includes the step of contacting synthesis gas having a ratio of hydrogen to carbon oxides of from about 0.1 to 10.0:1 over a combination catalyst at a reaction temperature of from about 100° C. to 500° C. and at a pressure of from about one atmosphere (0.1 MPa) to about 200 atmospheres (20 MPa) and at a gas hourly space velocity of from about 10 to 100,000. The combination catalyst itself comprises a medium to large port zeolite modified by the oxide or acid of an element selected from the group consisting of Group IIIA to VIIA elements and, a Fischer-Tropsch catalyst wherein the ratio of zeolite to Fischer-Tropsch component is from about 0.1 to 50:1.

A method is also provided for the preparation of a combination catalyst for the conversion of synthesis gas to saturated gaseous hydrocarbons. It includes the steps of modifying a medium to large port zeolite with an acid or oxide of a metal selected from the group consisting of Group IIIA to VIIA elements and combining the modified zeolite with a Fischer-Tropsch catalyst in a ratio of from about 0.1 to 50:1.

The method can include as further steps the calcining of the modified zeolite at temperatures ranging from about 100° to about 800° C. for at least one hour, prior to the combining of the zeolite and Fischer-Tropsch components, and reducing the combination catalyst with $H_2$ and/or CO at a temperature of from about 100° C. to 600° C., at $H_2$ and/or CO partial pressures ranging from 0.001 MPa to about 5.07 MPa and for a period of time of from about one to 100 hours prior to employing the catalyst for the conversion of synthesis gas.

The catalyst and process for its use results in a small liquid aromatic product also being formed which is suitable for forming gasoline. Olefins and oxygenates are essentially eliminated unlike the existing art where these occur.

PREFERRED MODE FOR CARRYING OUT THE INVENTION

The catalyst of the present invention comprises a mixture or combination of a Fischer-Tropsch catalyst and a medium or large port zeolite which has been modified with an oxide or acid selected from Group IIIA to Group VIIA of the Periodic Table.

The zeolites capable of use in this invention include medium port zeolites and large port zeolites. Examples of medium port zeolites include ferrierite, chabazite, erionite, ZSM-5 (U.S. Pat. No. 3,702,886) and ZSM-11 (U.S. Pat. No. 3,709,979). Examples of large port zeolites include mordenite, zeolite X (U.S. Pat. No. 2,882,244) and zeolite Y (U.S. Pat. No. 3,130,007). The foregoing list is exemplary only and is not intended to be limiting. A more complete description of the man-made zeolites can be found by referring to the cited patents, the subject matter of which is hereby incorporated by reference.

Pore opening diameter of such zeolites range from about 4 Å up to about 10 Å. The zeolites used should be in the $H^+$, or acid, form which may be prepared by a variety of methods known in the art. The zeolites are modified by impregnation with solutions, preferably aqueous or alcoholic solutions, of acids of the Groups IIIA to VIIA of the Periodic Table, preferably those of groups IIIA and VA and most preferably Group VA especially phosphorus. The acid can be from 1 to 50% of the zeolite on a weight basis and preferably between 10 and 40 weight percent.

The impregnated zeolite is subsequently dried and calcined at temperatures for at least one hour between 100 and 800° C. and preferably from 300 to 600° C. The calcined zeolite is then combined with a supported or unsupported Fischer-Tropsch catalyst, either as an intimate mixture or as separate particles. The Fischer-Tropsch catalysts include all of those generally known in the art. The catalysts employed in the examples were prepared according to the methods outlined in "The Fischer Tropsch and Related Syntheses" by H. H. Storch, N. Golumbic and R. B. Anderson, (John Wiley and Sons, Inc., 1951) the contents of which are incorporated herein by reference.

The ratio of zeolite to Fischer-Tropsch component may be from 0.1 to 50:1, preferably between 1 to 10:1. When the two components are combined as an intimate mixture, the powders of the components (greater than 30 mesh) are combined and thoroughly mixed in the desired ratio and a lubricant such as graphite can be added to the mix. One to two weight percent based upon the total catalyst weight is sufficient. The mixture is then pressed into pellets or wetted and extruded, followed by drying and calcination. Pelleted catalysts are broken into 10–30 mesh particles before placement into the reactor.

The catalyst is finally placed in the reactor and the Fischer-Tropsch component activated in a known manner such as by reduction with hydrogen, carbon monoxide or a combination with or without the presence of a diluent such as nitrogen. Reduction conditions are chosen to optimize the activity of the particular Fischer-Tropsch component present in the catalyst. They normally include heating to a temperature of at least 100° C. up to about 600° C. at $H_2$ and/or CO partial pressures ranging from 0.001 MPa to about 5.07 MPa and for a period of time of from about one to 100 hours.

In the process of the present invention, synthesis gas, i.e., a mixture of hydrogen and carbon monoxide, in a ratio of 0.1 to 10:1 $H_2$/CO and preferably 0.5 to 4:1 $H_2$/CO, is reacted in the presence of the novel catalyst in the vapor phase to form principally saturated gaseous hydrocarbons. The conversion can be conducted in either fluid bed or fixed bed reactors, the latter being exemplified herein, and the process is applicable to continuous or batch type operation.

The reaction temperature should be maintained between temperatures from about 100° to 500° C., preferably from about 150° to 350° C. Pressures may be from ambient to about 200 atmospheres (20 MPa), preferably from ambient to about 30 atmospheres (3 MPa). Synthesis gas space velocities can range from about 10 to 10,000 GHSV, or volumes of gas passed over one equivalent volume of catalyst per hour.

Products of the synthesis gas conversion resulting from practice of the present invention include gaseous alkanes having one to five carbon atoms. A small liquid fraction (<10 percent by volume) is sometimes produced containing significant amounts of aromatics and large amounts of isoparaffins. Such liquids could be useful as a blending stock for gasoline.

In the examples reported hereinbelow, catalysts of the present invention were prepared as follows:

Step I

Ten grams of crystalline ortho phosphoric acid was dissolved in 40 ml of water. The solution was added to 50 gms of Linde zeolite Y-82 (LZY-82) powder and the resulting mixture was stirred to form a thick paste. The paste was placed in an oven at 80° C. for four hours, subsequently dried at 150° C. overnight and then calcined overnight at 500° C. The modified zeolite is designated LZY-82-$H_3PO_4$ in the work which follows. Another acid form of zeolite was prepared with boric acid rather than phosphoric and has been designated LZY-82-$H_3BO_3$.

Step II

One part of the calcined LZY-82-$H_3PO_4$ was combined with one part of a Fischer-Tropsch catalyst comprising 75Fe(II):25Fe(III):20Cu(II). The solids were thoroughly mixed together and with 2 weight percent graphite. The mixture was pelleted, broken into 10 to 30 mesh particles and calcined at 500° C. for four hours. The catalyst is one of the present invention and is designated as Catalyst A.

One part of the calcined LZY-82-$H_3BO_3$ was similarly combined with one part of a Fischer-Tropsch catalyst comprising 75Fe(II):25Fe(III):20Cu(II). The solids were thoroughly mixed together and with 2 weight percent graphite. The mixture was pelleted, broken into 10 to 30 mesh particles and calcined at 500° C. for four hours. The catalyst is one of the present invention and is designated as Catalyst B.

Catalyst A was reduced and then run in a fixed bed reactor for the conversion of synthesis gas as follows: 20 cc of Catalyst A was placed in a fixed bed reactor and reduced at ambient pressure. 50 SCCM (standard cubic centimeters) of $H_2$, 50 SCCM of CO and 900 SCCM of $N_2$ were passed over the catalyst at 250° C. for 22.5 hours.

The bath temperature was then set to 241° C. and the pressure was increased to 1.04 MPa. Flows of 50 SCCM CO and 100 SCCM $H_2$ were introduced and a 983 minute run was conducted. A gas contraction of 21.4 percent was observed. The organic liquid recovered contained no detectable olefins or oxygenates while $2.8 \times 10^{-4}$ moles/gm of aromatics were obtained. NMR analysis showed a $CH_2/CH_3$ group ratio of 2.1. A similar reduction was given Catalyst B after which it was employed in a synthesis gas conversion, the results of which appear in the tables hereinbelow.

Additional synthesis gas conversions were run over the catalysts of the present invention in the manner just set forth and the results of all conversions are reported in the tables which appear hereinbelow.

For purposes of comparison, one catalyst not part of the present invention and designated Catalyst C was also prepared by combining an unmodified zeolite with a Fischer-Tropsch catalyst following the procedure of Step II hereinabove. The description of the preparation is as follows:

Catalyst C 1 part LZY-82 which had been calcined to give the H+ form and 1 part of 75Fe(II):25Fe(III):20Cu(II) were mixed and pelleted using the same procedure as Step II. 20 cc of Catalyst C was reduced at ambient pressure under a flow of 50 SCCM $H_2$, 50 SCCM CO and 900 SCCM $N_2$ at 250° C. for 22.5 hours. The pressure was then increased to 1.04 MPa and flows of 100 SCCM of $H_2$ and 50 SCCM of CO were fed at a bath temperature of 252° C. A run was conducted for 300 minutes and a contraction of 46.7 percent was observed. The organic liquid recovered was analyzed by NMR and contained olefins in the amount of $14.0 \times 10^{-4}$ moles per gram and aromatics in the amount of $2.9 \times 10^{-4}$ moles per gram. The $CH_2/CH_3$ ratio observed was 2.6.

Catalysts A and B were compared further against Catalyst C as well as one conventional Fischer-Tropsch catalyst composition which did not contain any zeolite. The catalysts evaluated included the following: Iron Fischer-Tropsch catalyst alone; Iron Fischer-Tropsch catalyst with zeolite, 50/50 mixture (Catalyst C); Iron Fischer-Tropsch catalyst with $H_3BO_3$ modified zeolite, 50/50 mixture (Catalyst B); and, Iron Fischer-Tropsch catalyst with $H_2PO_4$ modified zeolite, 50/50 mixture (Catalyst A). More specifically, the catalysts employed were as follows:

EXAMPLES NO. 1-4

75Fe(II):25Fe(III):20Cu(II)

EXAMPLES NO. 5-6

Catalyst C: 50%[75Fe(II):25Fe(III):20Cu(II)]/50%Y82

EXAMPLES NO. 7-9

Catalyst B: 50%[75Fe(II):25Fe(III):20Cu(II)]/50%LZY-82-$H_3BO_3$

EXAMPLES NO. 10-12

Catalyst A: 50%[75Fe(II):25Fe(III):20Cu(II)]/50%LZY-82-$H_3PO_4$

In each series of examples, 20 cc of a specific catalyst was selected, placed in the reactor after appropriate reduction of its Fischer-Tropsch component and then subjected to multiple runs with increasing time being reported in Table I.

The Fischer-Tropsch catalysts were reduced by subjecting 20 cc of the catalyst to a flow of $N_2$, $H_2$ and CO, 900 SCCM:50 SCCM:50SCCM, respectively for 22.5 hours at 250° C. and 1.04 MPa pressure. Reductions of the Fischer-Tropsch components of Catalysts A-C appear in Table I for the first numbered example following each new catalyst.

Reactions of synthesis gas over the catalysts were conducted under conditions set forth in Table I which reports grams of liquid organic product produced per hour. Analysis of the gas organic products was conducted and has been reported in Table II in mole percent. Gas contraction reported in Table I is determined as follows: [1-(volume gas out/volume gas in)]×100. Feed of synthesis gas is given as SCCM (standard cubic centimeters). Analysis of the liquid products by NMR was conducted and has been reported in Table III. The amounts present equal $1 \times 10^{-4}$ moles/gm of liquid. Lastly, Table IV presents per pass conversion and percent selectivity. Calculations of the percent of CO converted to a particular product (% ppc) and percent selectivity (% sel) for the gaseous products of Examples 8, 9, 11 and 12 were determined as follows:

% ppc=[moles of CO in product/moles of CO fed]×100

% sel=[SCCM product/SCCM CO (converted)]×100

TABLE I

| | Synthesis Gas Conversion Process | | | | | | | Total Liquid Organic |
|---|---|---|---|---|---|---|---|---|
| Ex. No. | T Bed | T exo | P gauge | GHSV | CO/$H_2$ | Contraction | Time | Product (gms/hr) |
| Fischer-Tropsch Catalysts Alone | | | | | | | | -- |
| 1 | 237 | 247 | 1.04 | 639 | 107/106 | 7% | 18 hr. | 0.17 |
| 2 | 237 | 247 | 1.04 | 900 | 107/212 | 16% | 4 hr. 32 min. | 0.19 |
| 3 | 250 | 262 | 1.04 | 250 | 50/50 | 31% | 18 hr. 10 min. | 0.33 |
| 4 | 250 | 261 | 1.04 | 375 | 107/52 | 22% | 21 hr. 38 min. | 0.05 |
| Catalyst C | | | | | | | | |
| 5 | 252 | 267 | 1.04 | 300 | 50/50 | 50% | 21 hr. 40 min. | 0.23 |
| 6 | 252 | 267 | 1.04 | 550 | 50/50 | 47% | 6 hr. 19 min. | 0.09 |
| Catalyst B | | | | | | | | |
| 7 | — | — | 0 | 900 | 0/300 | — | 22 hr. | — |
| 8 | 275 | 292 | 1.04 | 300 | 50/50 | 40.9% | 3 hr. 37 min. | 0 |
| 9 | 275 | 290 | 1.04 | 450 | 50/100 | 35.6% | 16 hr. 15 min. | 0 |
| Catalyst A | | | | | | | | |
| 10 | — | — | 0 | 900 | 0/300 | — | 19 hr. | — |
| 11 | 241 | 252 | 1.04 | 300 | 50/50 | 22.6% | 4 hr. | 0 |
| 12 | 241 | 250 | 1.04 | 450 | 50/100 | 21.4% | 16 hr. 23 min. | 0.03 |

TABLE II

Products From Synthesis Gas Conversion

| Ex. No. | CH$_4$ | CO$_2$ | C$_2$ | C$_2$= | C$_3$ | C$_3$= | C$_4$ | C$_4$= | iC$_4$ | iC$_4$= | cC$_4$= | tC$_4$= | C$_5$ | iC$_5$ | H$_2$ | CO |
|---|---|---|---|---|---|---|---|---|---|---|---|---|---|---|---|---|
| Fischer-Tropsch Catalysts Alone | | | | | | | | | | | | | | | | |
| 1 | 0.37 | 6.70 | 0.8 | .13 | .04 | .15 | .03 | .07 | — | — | — | — | — | — | 45 | 43 |
| 2 | 0.65 | 5.39 | .10 | .17 | .05 | .16 | .04 | .08 | — | — | — | — | — | — | 61 | 27 |
| 3 | 3.45 | 28.3 | 1.1 | .20 | .38 | .76 | .26 | .33 | — | .04 | .05 | .04 | — | — | 39 | 23 |
| 4 | 4.00 | 15.5 | 1.1 | .20 | .51 | .45 | .30 | .16 | — | .03 | .03 | .05 | — | — | 60 | 10 |
| Catalyst C | | | | | | | | | | | | | | | | |
| 5 | 7.86 | 44.5 | 3.5 | .16 | 1.93 | .85 | .57 | .12 | .17 | .06 | .24 | .41 | — | .18 | 31 | 10 |
| 6 | 9.13 | 24.21 | 3.38 | — | 2.2 | .14 | .73 | .03 | .14 | .03 | .09 | .17 | .23 | .15 | 60 | 1.3 |
| Catalyst B | | | | | | | | | | | | | | | | |
| 7 | — | — | — | — | — | — | — | — | — | — | — | — | — | — | — | — |
| 8 | 5.38 | 17.73 | 3.43 | — | 4.43 | — | 2.17 | — | 2.08 | — | — | — | 0.41 | 2.39 | — | 9.04 |
| 9 | 8.40 | 11.79 | 4.93 | — | 4.38 | — | 2.16 | — | 0.66 | — | — | — | — | 0.72 | — | — |
| Catalyst A | | | | | | | | | | | | | | | | |
| 10 | — | — | — | — | — | — | — | — | — | — | 13 | — | — | — | — | — |
| 11 | 2.17 | 4.41 | 1.70 | — | 1.81 | — | 1.02 | — | 0.50 | — | — | — | 0.04 | 0.81 | — | 34.37 |
| 12 | 3.54 | 3.07 | 2.36 | — | 2.23 | — | 1.27 | — | 0.33 | — | — | — | — | 0.35 | — | 35.13 |

TABLE III

Liquid Products From Synthesis Gas Conversion

| Ex. No. | CH$_2$/CH$_3$ | Vinyl Olefin | Internal Olefin | Vinylidene Olefin | Trisub Olefin | Ald. | Ester | Alc. | Acid | Ar. |
|---|---|---|---|---|---|---|---|---|---|---|
| 1 | 5.7 | 19.4 | 2.8 | 1.2 | 2.4 | 1.2 | 2.0 | 19.4 | 11.6 | 1.4 |
| 2 | 5.3 | 15.3 | 4.0 | 1.0 | 1.0 | 1.2 | 1.0 | 29.4 | 2.2 | 0.5 |
| 3 | 3.8 | 8.0 | 8.3 | 0.9 | 1.0 | — | 0.3 | 8.8 | 4.7 | 0.7 |
| 4 | 4.1 | 4.4 | 8.1 | 0.9 | 1.0 | — | — | 15.1 | 12.2 | 0.9 |
| 5 | 1.7 | — | 45.2 | 7.5 | 45.1 | — | — | — | — | 11.8 |
| 6 | 2.6 | — | 5.8 | 1.7 | 6.6 | — | — | — | — | 2.9 |
| 12 | 2.1 | 0 | 0 | 0 | 0 | 0 | 0 | 0 | 0 | 2.8 |

TABLE IV

Conversion of CO and Selectivity of Catalysts A and B

| | 8 - Catalyst B | | | 9 - Catalyst B | | | 11 - Catalyst A | | | 12 - Catalyst A | | |
|---|---|---|---|---|---|---|---|---|---|---|---|---|
| Products | SCCM | % PPC | % SEL | SCCM | % PPC | % SEL | SCCM | % PPC | % SEL | SCCM | % PPC | % SEL |
| CO (conv) | 40.96 | — | — | 32.52 | — | — | 15.63 | — | — | 14.87 | — | — |
| CO | 9.04 | — | — | 17.48 | — | — | 34.37 | — | — | 35.13 | — | — |
| CO$_2$ | 17.73 | 35.46 | 43.28 | 11.79 | 23.58 | 36.25 | 4.41 | 8.82 | 28.21 | 3.07 | 6.14 | 20.64 |
| CH$_4$ | 5.38 | 10.76 | 13.13 | 8.40 | 16.80 | 25.83 | 2.17 | 4.34 | 13.88 | 3.54 | 7.08 | 23.81 |
| C$_2$H$_6$ | 3.43 | 6.86 | 8.37 | 4.93 | 9.66 | 19.70 | 1.70 | 3.40 | 10.88 | 2.36 | 4.72 | 15.87 |
| C$_2$H$_4$= | — | — | — | — | — | — | — | — | — | — | — | — |
| C$_3$H$_8$ | 4.43 | 8.86 | 10.81 | 4.38 | 8.76 | 13.47 | 1.81 | 3.62 | 11.58 | 2.23 | 4.46 | 15.00 |
| C$_3$H$_6$= | — | — | — | — | — | — | — | — | — | — | — | — |
| i-C$_4$H$_{10}$ | 2.08 | 4.16 | 5.08 | 0.66 | 1.32 | 2.03 | 0.50 | 1.00 | 3.20 | 0.33 | 0.66 | 2.22 |
| nC$_4$H$_{10}$ | 2.17 | 4.34 | 5.30 | 2.16 | 4.32 | 6.54 | 1.02 | 2.04 | 6.53 | 1.27 | 2.54 | 8.54 |
| 1-C$_4$H$_8$= | — | — | — | — | — | — | — | — | — | — | — | — |
| i-C$_4$H$_8$= | — | — | — | — | — | — | — | — | — | — | — | — |
| t-C$_4$H$_8$= | — | — | — | — | — | — | — | — | — | — | — | — |
| c-C$_4$H$_8$= | — | — | — | — | — | — | — | — | — | — | — | — |
| i-C$_5$H$_{12}$ | 2.39 | 4.78 | 5.83 | 0.72 | 1.44 | 2.21 | 0.81 | 1.62 | 5.18 | 0.35 | 0.70 | 2.35 |
| nC$_5$H$_{12}$ | 0.41 | 0.82 | 1.00 | — | — | — | 0.04 | 0.08 | 0.26 | — | — | — |
| Liq. gas equiv. | — | — | — | — | — | — | — | — | — | — | 1.70 | 5.71 |

With reference to Tables I–III, it can be noted that the standard Fischer-Tropsch catalyst produced relatively low amounts of saturated gaseous alkanes, a fair amount of unsaturated gases, a high amount of liquid olefins and oxygenates and, little to no aromatics. Catalyst C also produced a fair amount of unsaturated gases and considerable liquid olefins where a 1:1 CO/H$_2$ feed was employed (Ex. No. 5). Liquid oxygenates were eliminated and aromatic content was significantly higher. The catalysts of the invention, Catalysts A and B, produced the greatest amount of saturated gases, essentially no unsaturates, gas or liquid, no oxygenates and a lesser amount of aromatics.

The CH$_2$/CH$_3$ ratio can be used to determine the chain length or extent of branching. When this number is compared with boiling point fraction data (not reported herein), it is possible to determine branching. Generally speaking a ratio of less than 2.5 is good for gasoline fractions and 2.0 is excellent. A value of 2.1 was observed for Example 12, Catalyst A, and hence, the small liquid organic material produced would be usable for gasoline production or upgrading.

Based upon the satisfactory yields of saturated gaseous hydrocarbons and minimal amounts of olefins and oxygenates that have been obtained when the catalyst of the present invention has been employed in the process set forth herein, it should be apparent that the objects of the invention have been met. It is to be understood that the catalyst of the present invention can be modified with oxides or acids of other elements from Groups IIIA to VIIA than the two exemplified herein. Similarly, other Fischer-Tropsch catalysts can be employed.

It should also be apparent to those skilled in the art that the process of the subject invention is operable with catalysts having fairly broad ratios of modifier to zeolite and of zeolite to Fischer-Tropsch catalyst and that the process is operable when other temperatures, pressures and times are employed. It is to be understood that these variables fall within the scope of the claimed invention and that the subject invention is not to be limited by the examples set forth herein. These have been provided merely to demonstrate operability and, therefore, the selection of specific catalyst components and process conditions can be determined without departing from the spirit of the invention herein disclosed and described. Moreover, the scope of the invention shall include all modifications and variations that may fall within the scope of the attached claims.

We claim:

1. A process for producing fuel grade saturated gaseous hydrocarbons comprising the steps of:
   contacting synthesis gas having a ratio of hydrogen to carbon oxides of from about 0.1 to 10.0:1 over a combination catalyst at a reaction temperature of from about 100° C. to 500° C. and at a pressure of from about 0.1 MPa to about 20 MPa and at a gas hourly space velociy of from about 10 to 100,000, said combination catalyst comprising
   a medium to large port zeolite having a pore opening diameter of from about 4Å to 10Å, said zeolite being modified by the oxide or acid of an element selected from the group consisting of boron and Group VA elements; and
   a Fischer-Trpsch catalyst wherein the ratio of zeolite to Fischer-Tropsch component is from about 0.1 to 50:1.

2. A process, as set forth in claim 1, wherein the amount of said oxide or acid present in said modified zeolite comprises from about one to 50 percent by weight.

3. A process, as set forth in claim 2, wherein said zeolite is modified with phosphoric acid in an amount of 20 percent by weight and said modified zeolite is combined with an equal amount by weight of said Fischer-Tropsch catalyst.

4. A process, as set forth in claim 3, wherein said Fischer-Tropsch catalyst comprises 75Fe(II):25Fe(III): 20Cu(II).

5. A process, as set forth in claim 4, further comprising at least about one percent by weight of a lubricant.

6. A process, as set forth in claim 5, wherein said lubricant is graphite.

7. A process, as set forth in claim 2, wherein said zeolite is modified with boric acid in an amount of 14 percent by weight and said modified zeolite is combined with an equal amount by weight of said Fischer-Tropsch catalyst.

8. A process, as set forth in claim 7, wherein said Fischer-Tropsch catalyst comprises 75Fe(II):25Fe(III): 20Cu(II).

9. A process, as set forth in claim 8, further comprising at least about one percent by weight of a lubricant.

10. A process, as set forth in claim 9, wherein said lubricant is graphite.

11. A process, as set forth in claim 1, wherein said synthesis gas composition is 2:1 $H_2/CO$.

12. A process, as set forth in claim 11, wherein said temperature is about 250° C., said pressure is 1.04 MPa and said GHSV is 450.

13. A process, as set forth in claim 1, wherein said synthesis gas composition is 1:1 $H_2/CO$.

14. A process, as set forth in claim 13, wherein said temperature is about 250° C., said pressure is 1.04 MPa and said GHSV is 300.

15. A process, as set forth in claim 13, comprising the further step of:
   reducing said combination catalyst with $H_2$ and/or CO at a temperature of from about 100° C. to 500° C., at $H_2$ and/or CO partial pressures ranging from 0.001 MPa to about 5.07 MPa and for a period of time of from about one to 100 hours prior to said step of contacting.

* * * * *